(12) United States Patent
Wedan

(10) Patent No.: US 7,853,318 B2
(45) Date of Patent: Dec. 14, 2010

(54) CARDIAC SENSING BY IMPLANTABLE MEDICAL DEVICES DURING MAGNETIC RESONANCE IMAGING

(75) Inventor: Steven R. Wedan, Savage, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 942 days.

(21) Appl. No.: 11/686,159

(22) Filed: Mar. 14, 2007

(65) Prior Publication Data

US 2008/0228092 A1 Sep. 18, 2008

(51) Int. Cl.
*A61B 5/04* (2006.01)
(52) U.S. Cl. ...................................... 600/509
(58) Field of Classification Search ............. 324/76.42; 600/508, 509; 607/7, 8, 60
See application file for complete search history.

(56) References Cited

U.S. PATENT DOCUMENTS

| | | | |
|---|---|---|---|
| 4,301,804 A | 11/1981 | Thompson et al. | |
| 4,379,459 A | 4/1983 | Stein | |
| 4,745,284 A | 5/1988 | Masuda et al. | |
| 4,991,580 A | 2/1991 | Moore | |
| 5,038,785 A | 8/1991 | Blakeley et al. | |
| 5,074,309 A | 12/1991 | Gerdt | |
| 5,217,010 A | 6/1993 | Tsitlik et al. | |
| 5,347,222 A | 9/1994 | Fox et al. | |
| 5,540,724 A * | 7/1996 | Cox ............................ | 607/8 |
| 5,601,607 A | 2/1997 | Adams | |

(Continued)

FOREIGN PATENT DOCUMENTS

EP 1716878 11/2006

(Continued)

OTHER PUBLICATIONS

Abi-Abdallah, Dima et al., "Reference signal extraction from corrupted ECG using wavelet decomposition for MRI sequence triggering: application to small animals", *BioMedical Engineering OnLine* www.biomedical-engineering-online.com/content/5/1/11 Feb. 20, 2006, 1-12.

(Continued)

*Primary Examiner*—George Manuel
*Assistant Examiner*—Robert N Wieland
(74) *Attorney, Agent, or Firm*—Pauly, DeVries Smith & Deffner, L.L.C.

(57) ABSTRACT

Embodiments of the invention can include a method for reducing MRI interference from a physiological electrical signal received in an implantable medical device. The method can include the steps of amplifying the physiological electrical signal with a high bandwidth amplifier and sampling the amplified physiological electrical signal at a sampling frequency of at least 8 kHz to obtain a first high-frequency sequence of samples. The method can further includes the steps of processing the first high-frequency sequence of samples to identify a signal artifact that is characteristic of MRI interference and creating a second high-frequency sequence of samples by reducing the signal artifact characteristic of MRI interference from the first sequence of samples. Embodiments can also include a method of determining a heart rate from a physiological electrical signal received in an implantable medical device. Embodiments can also includes an implantable medical device that receives and processes a physiological electrical signal. Other embodiments are also described herein.

22 Claims, 5 Drawing Sheets

U.S. PATENT DOCUMENTS

| | | | |
|---|---|---|---|
| 5,968,083 | A | 10/1999 | Ciciarelli et al. |
| 6,016,446 | A | 1/2000 | Belalcazar |
| 6,198,972 | B1 | 3/2001 | Hartlaub et al. |
| 6,427,085 | B1 | 7/2002 | Boon et al. |
| 6,641,541 | B1 * | 11/2003 | Lovett et al. ............... 600/508 |
| 6,925,322 | B2 | 8/2005 | Helfer et al. |
| 6,954,674 | B2 | 10/2005 | Connelly |
| 7,015,393 | B2 | 3/2006 | Weiner et al. |
| 7,020,517 | B2 | 3/2006 | Weiner |
| 7,038,601 | B2 | 5/2006 | Uutela et al. |
| 7,050,855 | B2 | 5/2006 | Zeijlemaker et al. |
| 7,076,283 | B2 | 7/2006 | Cho et al. |
| 7,082,328 | B2 | 7/2006 | Funke |
| 7,091,412 | B2 | 8/2006 | Wang et al. |
| 7,123,013 | B2 | 10/2006 | Gray |
| 2002/0163333 | A1 | 11/2002 | Schlicker et al. |
| 2003/0083570 | A1 | 5/2003 | Cho et al. |
| 2003/0140931 | A1 | 7/2003 | Zeijlemaker et al. |
| 2003/0144704 | A1 | 7/2003 | Terry et al. |
| 2003/0176897 | A1 | 9/2003 | Stessman |
| 2004/0088012 | A1 | 5/2004 | Kroll et al. |
| 2004/0098093 | A1 | 5/2004 | DiCarlo |
| 2004/0135571 | A1 * | 7/2004 | Uutela et al. ............... 324/76.42 |
| 2004/0263172 | A1 | 12/2004 | Gray et al. |
| 2005/0070975 | A1 | 3/2005 | Zeijlemaker et al. |
| 2006/0155268 | A1 | 7/2006 | Amir et al. |
| 2006/0293591 | A1 | 12/2006 | Wahlstrand et al. |
| 2007/0191914 | A1 | 8/2007 | Stessman |
| 2008/0147135 | A1 * | 6/2008 | Hareland ....................... 607/7 |
| 2008/0195180 | A1 * | 8/2008 | Stevenson et al. ............. 607/60 |

FOREIGN PATENT DOCUMENTS

| | | |
|---|---|---|
| WO | WO-03037429 | 5/2003 |

OTHER PUBLICATIONS

Fontaine, John M. et al., "Rapid Ventricular Pacing in a Pacemaker Patient Undergoing Magnetic Resonance Imaging", *PACE*, vol. 21 Jun. 1998, pp. 1336-1339.

Luechinger, Roger et al., "In Vivo Heating of Pacemaker Leads During Magnetic Resonance Imaging", *European Heart Journal, The European Society of Cardiology* 2004 pp. 1-8.

EP Office Action for related pending application No. 08730844.1, mailed Mar. 19, 2010 (2 pages).

File History for co-pending U.S. Appl. No. 11/684,419, filed Mar. 9, 2007, downloaded from USPTO Website Jun. 23, 2010 (28 pages).

File History for co-pending U.S. Appl. No. 11/680,267, filed Feb. 28, 2007, downloaded from USPTO Website Jun. 23, 2010 (54 pages).

International Search Report, mailed Oct. 8, 2008, from International application No. PCT/US2008/055127, filed Mar. 6, 2008 (13 pages).

International Search Report, mailed Jul. 17, 2008, from International application No. PCT/US2008/056015, filed Mar. 6, 2008 (17 pages).

* cited by examiner

CARDIAC SENSING BY IMPLANTABLE MEDICAL DEVICES DURING MAGNETIC RESONANCE IMAGING

FIELD OF THE INVENTION

The invention relates to cardiac rhythm management devices, and more particularly, to the sensing of cardiac activity by implantable cardiac rhythm management devices during magnetic resonance imaging (MRI).

BACKGROUND OF THE INVENTION

Many different types of medical devices are implanted within patients to provide medical therapy. One type of implanted medical device is a cardiac rhythm management device, such as a pacemaker or implantable defibrillator. Cardiac rhythm management (CRM) devices are used to provide medical therapy to patients who have a disorder related to cardiac rhythm, such as bradycardia or tachycardia.

Magnetic resonance imaging (MRI) is a method of visualizing body tissues of a patient, primarily to identify pathological conditions or to visualize physiological structure for purposes of medical diagnosis and therapy. MRI relies on subjecting the body tissue of interest to a very strong uniform magnetic field, up to about 30,000 gauss, as well as a moderate strength but variable magnetic field of around 200 gauss. In the presence of these uniform and gradient magnetic fields, a radio frequency (RF) pulse is transmitted from a coil to the body tissue. Hydrogen atoms within the body tissue have a magnetic moment and tend to line up with the direction of the applied magnetic fields. Some of these hydrogen atoms will align facing one direction and others will align facing an opposite direction, such that most of the hydrogen atoms facing in alternating directions will tend to cancel each other out. However, a small percentage (but a significant absolute number) of hydrogen atoms will be unbalanced, or not cancelled out. The applied RF pulse tends to cause the unbalanced hydrogen protons to spin, or resonate, in a particular direction and at a particular frequency. When this RF pulse is turned off, the spinning hydrogen protons revert to their earlier, aligned position, and release their excess energy. The RF coil of the MRI machine is capable of detecting this emitted energy and transmitting a corresponding signal to a processor that transforms the signal to an image of the body tissue. Because different tissues have different characteristic responses to the application of the RF pulse in the presence of the magnetic fields, these differences can be utilized to prepare an image showing areas of contrasting tissue types.

MRI techniques have proven to be very effective at diagnosing certain medical conditions and allowing for patients to receive timely, appropriate medical therapy. However, in many cases patients having an implanted medical device are contraindicated for MRI, and therefore may be unable to benefit from the full scope of medical treatments available to them. One problem is that the MRI's RF field can induce a high frequency current within the implanted device, and this high frequency current can result in tissue heating. In certain circumstances the tissue heating can cause serious injury to the patient. Another and potentially very serious problem for a patient having certain implanted medical devices, particularly a cardiac rhythm management device, is the potential for the MRI machine to create a low frequency induced current (LFIC) in the implanted device. LFIC arises from the interaction between the MRI system's time-varying magnetic gradient fields and any conductive loop associated with the implanted device. LFIC in a CRM device can actually cause pacing of the heart by activating nerve or muscle cells within the heart. In this way, it is possible for the MRI machine to inadvertently pace the patient's heart. The LFIC can also distort the wave shape of intended pacing pulses, possibly resulting in a diminished effectiveness of the pacing pulse.

Importantly, LFIC can also interfere with the pacemaker system's ability to properly sense cardiac activity, possibly resulting in inhibited pacing or pacing that is too rapid. Pacing that is inhibited or too rapid can cause injury or discomfort to a patient. Some CRM devices are configured to be manually set to an asynchronous mode during an MRI procedure, where the CRM device is configured to deliver pacing at a constant rate regardless of sensed heart rate. In essence, the sensing capabilities of the CRM device are turned off while in the MRI machine. While this technique addresses the MRI-induced interference with the sensed signals, it does not provide optimal pacing to the patient. For example, a patient who experiences fibrillation while undergoing an MRI procedure will not receive the therapy that an implanted device may be configured to deliver.

Improved techniques for using an implantable medical device for sensing a patient's heart rate are needed.

SUMMARY OF THE INVENTION

In one aspect, the invention relates to a method for reducing MRI interference from a physiological electrical signal received in an implantable medical device. The method includes the steps of amplifying the physiological electrical signal with a high bandwidth amplifier of an implantable medical device having a bandwidth equal to or greater than about 4 kHz and sampling the amplified physiological electrical signal at a sampling frequency equal to or greater than about 8 kHz to obtain a first high-frequency sequence of samples. The method further includes the steps of processing the first high-frequency sequence of samples to identify a signal artifact that is characteristic of MRI interference and creating a second high-frequency sequence of samples by reducing the signal artifact characteristic of MRI interference from the first sequence of samples. The second high-frequency sequence generally includes samples having a constant time interval between them as characteristic of a constant sampling rate and generally has no samples missing or repeated.

Another aspect of the invention relates to a method of calculating a heart rate from a physiological electrical signal received in an implantable medical device. The method includes the steps of amplifying the physiological electrical signal with a high bandwidth amplifier of an implantable medical device having a bandwidth equal to or greater than about 4 kHz and sampling the amplified physiological electrical signal at a sampling frequency equal to or greater than about 8 kHz to obtain a first high-frequency sequence of samples. The method further includes the steps of processing the first high-frequency sequence of samples to identify a superposed signal artifact that is characteristic of MRI interference and reducing the superposed signal artifact from the first high-frequency sequence of samples to form a second high-frequency sequence of samples. The method also includes the step of processing the second high-frequency sequence of samples to identify the timing of heart contractions.

A further aspect of the invention relates to a method of determining a heart rate from a physiological electrical signal received in an implantable medical device. The method includes the steps of receiving an input associated with the presence of an environment that tends to cause corruption of a physiological electrical signal and initiating a mode of operation for reducing corruption of the physiological electrical signal. The mode of operation includes the steps of amplifying the physiological electrical signal with a high bandwidth amplifier of an implantable medical device having a bandwidth of equal to or greater than about 4 kHz, sampling the amplified physiological electrical signal at a sampling frequency equal to or greater than about 8 kHz to obtain a first high-frequency sequence of samples, processing the first high-frequency sequence of samples to identify a superposed signal artifact characteristic of MRI interference, reducing the superposed signal artifact component of the first high-frequency sequence of samples to form a second high-frequency sequence of samples, and processing the second high-frequency sequence of samples to identify the timing of heart contractions.

Yet another aspect of the invention relates to an implantable medical device that receives and processes a physiological electrical signal. The implantable medical device includes a conductor for transmitting the physiological electrical signal from body tissue to the implantable medical device and physiological signal processing circuitry for identifying heart contractions from the physiological electrical signal. The signal processing circuitry includes a high bandwidth amplifier having a bandwidth of equal to or greater than 4 kHz for amplifying the physiological electrical signal received from the conductor, a high frequency analog to digital converter for sampling the amplified physiological electrical signal at a sampling frequency equal to or greater than about 8 kHz to obtain a first high-frequency sequence of samples, a digital signal processor configured to process the first high-frequency sequence of samples to identify a superposed signal artifact characteristic of MRI interference and further configured to reduce the superposed signal artifact from the first high-frequency sequence of samples to form a second high-frequency sequence of samples, and cardiac activity detection circuitry configured to process the second high-frequency sequence of samples to identify heart contractions.

The invention may be more completely understood by considering the detailed description of various embodiments of the invention that follows in connection with the accompanying drawings.

Figure 1:
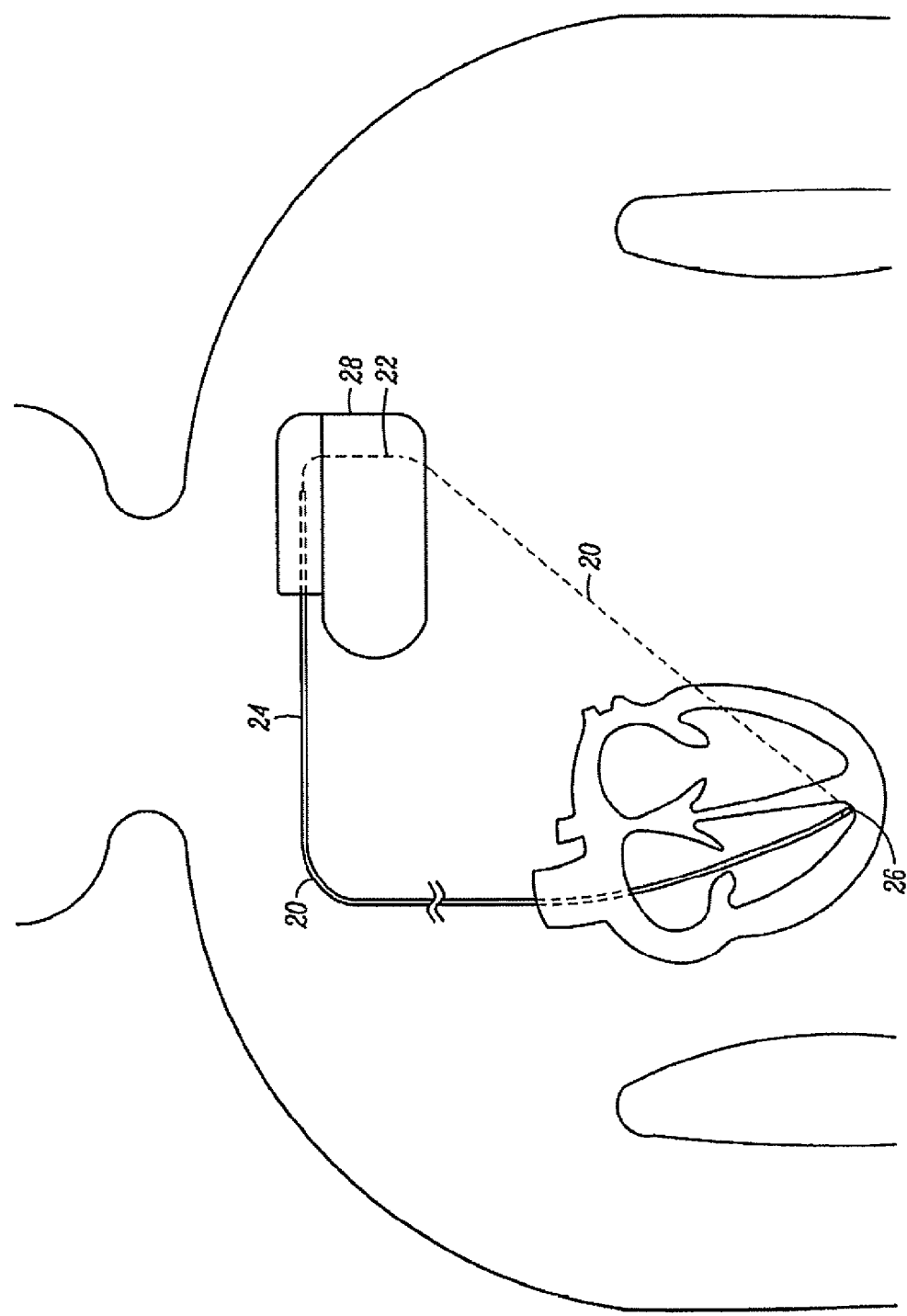
FIG. 1 is a schematic view of a conductive loop formed in an implanted unipolar cardiac pacing device.

While the invention may be modified in many ways, specifics have been shown by way of example in the drawings and will be described in detail. It should be understood, however, that the intention is not to limit the invention to the particular embodiments described. On the contrary, the intention is to cover all modifications, equivalents, and alternatives following within the scope and spirit of the invention as defined by the claims.

DETAILED DESCRIPTION OF THE INVENTION

A variety of implanted medical devices are used to provide a variety of medical therapies to patients. One example of such an implanted medical device is a cardiac rhythm management (CRM) device, often used to manage cardiac conditions such as bradycardia and tachycardia. A specific example of a CRM device is a pacemaker, which can include a pulse generator for generating a pacing pulse and one or more leads for delivering the pacing pulse to the cardiac tissue. Pacemakers can be configured to sense the electrical activity of the patient's heart, as transmitted through the leads. In some pacing modes, if the pacemaker does not detect electrical activity above a certain trigger threshold within a certain time interval, the pacemaker will deliver a pacing pulse through the one or more leads to the cardiac tissue. This pacing pulse causes the heart to beat. In some devices such as an implantable defibrillator, the detection of an excessive heart rate causes a shock to be delivered to the cardiac tissue to attempt to restore a normal heart rhythm.

A key performance issue of any CRM device is battery life. Battery voltage below a certain level can prevent the device from functioning properly or reliably, and battery replacement involves surgery, which is inconvenient, expensive, and associated with risk. Therefore, it is desired to minimize the current consumed within the pacemaker to extend the battery life. Toward this end, CRM devices are generally configured to sample cardiac electrical activity at a relatively low rate (frequency). Low sampling rates require less energy over a given period of time than higher sampling rates. Therefore, the low sampling rate typical of CRM devices conserves battery life and extends the time before a battery replacement surgery is required.

Magnetic resonance imaging relies on the creation of time varying magnetic field gradients within a patient's body. The body of a patient undergoing an MRI exam is not subject to a uniform magnetic field, but rather is subject to a magnetic field that is different at each location of the patient's body and that varies continuously with time. Faraday's law states that any change in a magnetic field around a conductive loop will cause a voltage to be induced in the conductive loop, and consequently, cause a current to flow in the conductive loop. As per Faraday's law, the time varying magnetic field gradients in the body of a patient undergoing an MRI procedure generate a voltage, and consequently a current, in any conductive loop present within the time varying magnetic field. In the case of a patient having an implanted CRM device and undergoing an MRI procedure, the time varying magnetic field gradient of the MRI machine creates the required changing magnetic field and the implanted pacemaker or other cardiac rhythm management device forms the conductive loop. The induced currents can include those with a frequency of less than about 20 kHz, sometimes referred to as "low frequency induced currents" (LFIC) because their frequency is low relative to radiofrequency induced currents which can have a frequency in the megahertz range. LFIC can interfere with the functioning of an implanted medical device. For example, it is possible that LFIC could cause pacing of the heart by activating nerve or muscle cells within the heart. In this way, it may be possible for the MRI machine to inadvertently pace the patient's heart. The LFIC can also distort the waveshape of intended pacing pulses, possibly resulting in a diminished effectiveness of the pacing pulse. LFIC can further interfere with the pacemaker system's ability to properly sense cardiac activity, possibly resulting in inhibited pacing or rapid pacing.

In a unipolar pacemaker system such as that depicted in FIG. 1, a loop 20 is formed from the pacemaker internal circuitry 22, through the lead 24 to the electrode 26 in contact with cardiac tissue, and then through body tissue back to the pacemaker housing 28. The area enclosed by this loop is significant and therefore a substantial amount of LFIC can be generated within this loop by the time varying magnetic field gradients of an MRI system.

Figure 2:
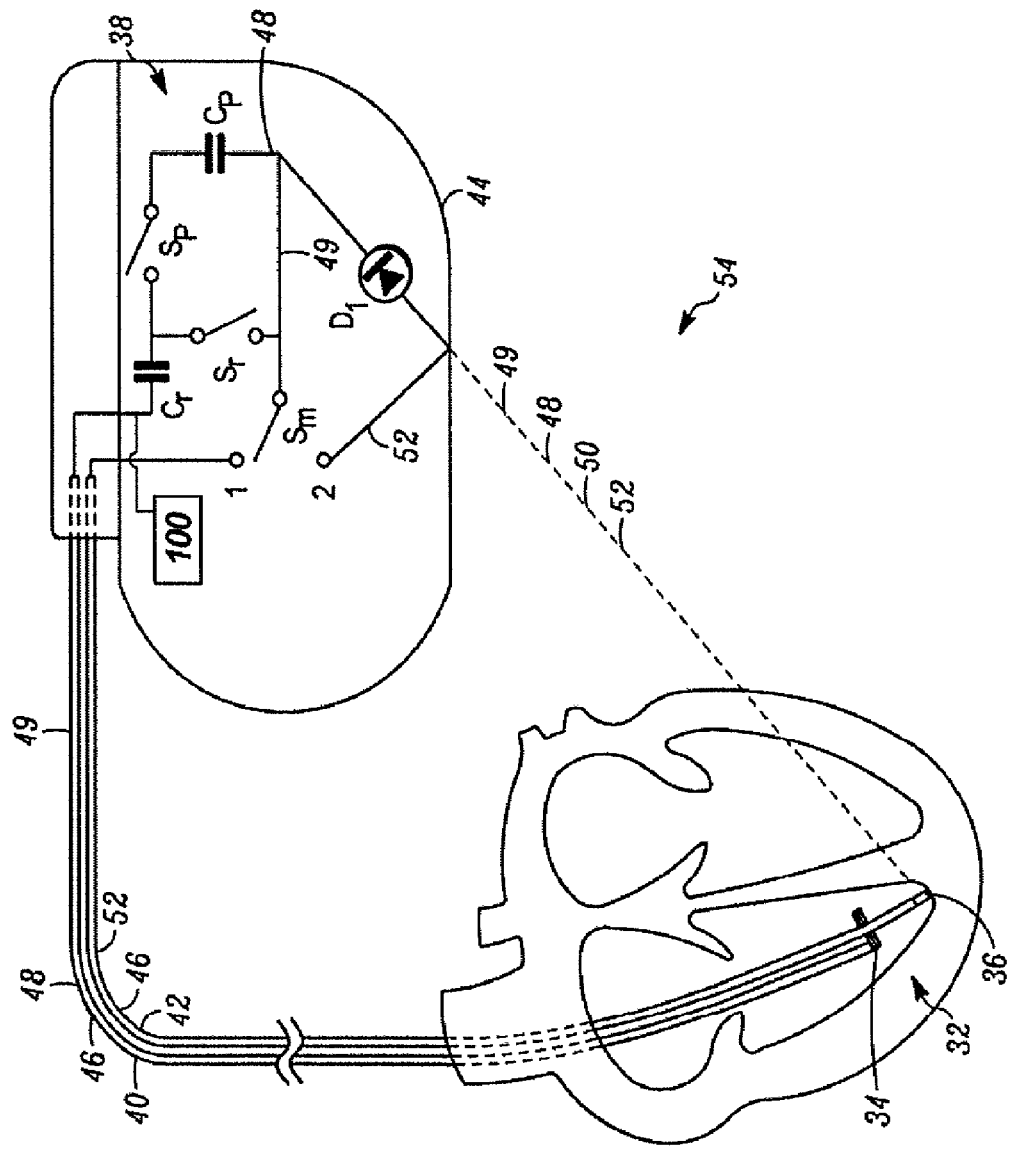
FIG. 2 is a schematic view of a conductive loop formed in an implanted bipolar cardiac pacing device.

Conductive loops can also be created in the context of bipolar pacing systems. FIG. 2 shows a simplified schematic diagram of some aspects of a typical bipolar pacemaker system. Bipolar pacemaker 54 includes a tip and ring electrode 32, where the tip electrode 36 and ring electrode 34 are each implanted in cardiac tissue, but are separated by a relatively small distance from each other. Pacemaker 54 can include various circuitries, such as pulse generation circuitry, sensing circuitry, charging circuitry, control circuitry, and the like. Sensing circuitry, charging circuitry, and control circuitry (not shown in FIG. 2) can be constructed according to principles known to those of skill in the art. In FIG. 2, pulse generator 38 includes pacing switch $S_p$, pacing capacitor $C_p$, recharging switch $S_r$, and recharging capacitor $C_r$. A housing 44 is provided that contains pulse generator 38. The housing 44 can be constructed of a conductive material.

As shown in FIG. 2, pulse generator 38 also includes switch $S_m$ for switching between bipolar mode and unipolar mode. To select a unipolar mode of operation, switch $S_m$ is configured to connect the pacemaker housing 44 to the pulse generator 38 circuitry. In the unipolar mode of operation, the tip electrode 36 generally serves as the cathode and the housing 44 itself serves as the anode. In FIG. 2, this occurs where switch $S_m$ connects to terminal 2 of switch $S_m$. To select a bipolar operation mode, switch $S_m$ is configured to connect conductor 42 to the pulse generator 38 circuitry. In the bipolar mode of operation, the tip electrode 36 generally serves as the cathode and the ring electrode 34 generally serves as the anode. In the embodiment of FIG. 2, this occurs when switch $S_m$ connects to terminal 1 of switch $S_m$.

In bipolar capable pacemakers, there is generally more than one conductive loop in which current can be induced. In bipolar mode, a first loop 46 is formed when either switch $S_p$ or switch $S_r$ is closed, the first loop 46 being formed either through switch $S_r$ or capacitor $C_p$ and switch $S_p$, through capacitor $C_r$, through first conductor 40 and tip electrode 36, through cardiac tissue into ring electrode 34, and through second conductor 42 to switch $S_m$. However, first and second conductors 40, 42 are generally very close together, such as disposed together within one lead. Therefore, conductive loops that include both first conductor 40 and second conductor 42 generally enclose a very small area and therefore induced current in these loops is usually insignificant.

However, conductive loops enclosing a relatively large area can also be formed by some bipolar pacemakers. Many bipolar pacemakers include an integrated circuit protection diode $D_1$. Diode $D_1$ allows current to flow from the pacemaker housing 44 into the pulse generator circuitry to the reference potential (ground) of capacitor $C_p$. This is useful to prevent the pacemaker ground from deviating from the pacemaker housing potential. However, this diode $D_1$ can facilitate the formation of conductive loops within the pacemaker. For example, when switch $S_p$ is closed, loop 48 is formed passing through capacitor $C_p$, switch $S_p$, capacitor $C_r$, conductor 40, tip electrode 36, tissue path 50, back to housing 44 and through diode $D_1$. When switch Sr is closed, loop 49 is formed passing through switch Sr, capacitor Cr, conductor 40, tip electrode 36, tissue path 50, back to housing 44 and through diode $D_1$. Loops 48 and 49 can be formed regardless of the position of switch $S_m$.

Furthermore, when switch $S_m$ is in bipolar mode, another conductive loop 52 can be formed regardless of the positions of switches $S_r$ and $S_p$. Conductive loop 52 can be formed passing through second conductor 42, electrode 36, tissue path 50 to housing 44, through diode $D_1$, and back to second conductor 42 through switch $S_m$. Loops 48, 49, and 52 each enclose an area sufficiently large to make the generation of LFIC during MRI a concern.

Figure 3:
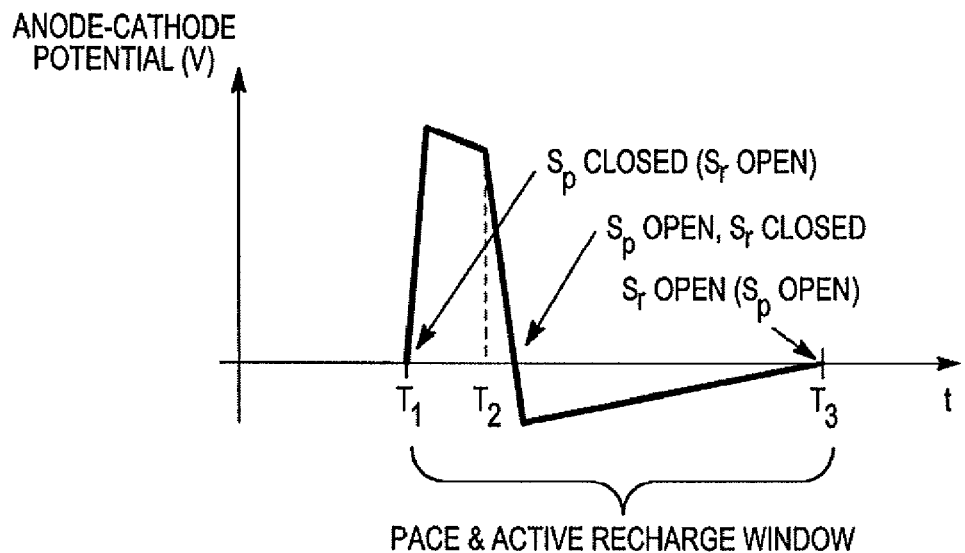
FIG. 3 is a diagram of an idealized pacing pulse.
Figure 4:
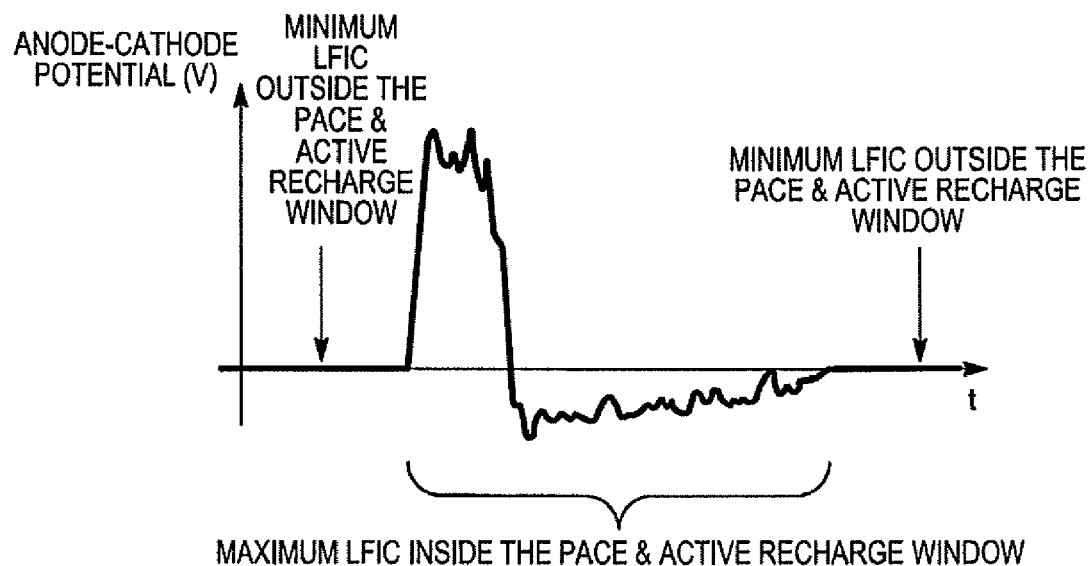
FIG. 4 is a diagram of a pacing pulse affected by low frequency induced current.

LFIC can have harmful effects on the patient. If the induced current is large enough, the current can cause activation of the heart muscle. The induced current can also cause distortion of a pacing pulse sent from the pacemaker through the leads to the heart. For example, FIG. 3 shows an example of an idealized pacing pulse. At a first time $T_1$, a pacing switch is closed causing a current pulse to be delivered through the leads for a period of time, until at time $T_2$ the pacing switch is opened and the current pulse diminishes. Also at time $T_2$, a charging switch is closed to allow charging of a capacitor until time $Tt_3$ when the charging switch is opened. FIG. 4 shows an example of how an idealized pacing pulse can be affected by the presence of LFIC. The current that is induced into the loop will add to or subtract from the voltage of the pacing pulse, resulting in a distorted pulse, such as that seen in FIG. 4. In some cases, the induced distortion may cause the electrical pulse to be insufficient to capture the patient's heart. In some cases, the LFIC may be large enough in magnitude to capture the patient's heart at times other than during the pacing pulse. For example, by forward biasing diode $D_1$, capture outside of the pace and active recharge window can be facilitated. In any case, the LFIC can interfere with the proper operation of the pacing device, possibly causing injury to the patient.

A CRM device typically senses the electrical activity of the patient's heart through leads that are implanted in the cardiac tissue that provide an electrically conductive path to the CRM device and its associated circuitry. In normal heart operation, the sinoatrial (SA) node initiates an action potential that is transmitted to the cardiac tissue of the left and right atria, and also to the atrioventricular (AV) node, where the action potential is delayed before being transmitted to the cardiac tissue of the left and right ventricle. A lead of a CRM device is placed so that it is in contact with the myocardium, such that the electrical potential is transmitted through the lead to the CRM device circuitry. This electrical potential can be called a cardiac signal. The cardiac signal is an analog signal.

It is desired to be able to sense the patient's cardiac activity regardless of the presence of interference associated with an MRI environment. A CRM device is typically configured to sense for a patient's heart beat at a very low sampling rate, on the order of 200 Hz. At this relatively low sampling rate, LFIC can confuse the sensing circuitry, possibly causing a heart beat to go undetected or causing the sensing circuitry to detect a heart beat when one did not actually exist. This can cause the CRM device to deliver therapy that is not appropriate or to not deliver therapy that is needed.

As described above, a cardiac electrical activity signal taken from a patient who is undergoing an MRI exam will be distorted by the presence of low frequency induced current. However, because a typical CRM device samples at a relatively low rate, such as about 200 Hz, the CRM device does not necessarily sense the LFIC and its associated non-linearities and spikes in the signal. Rather, in some cases, the CRM device will see a smoothed trace that is reflective of the fact that the frequency of the distorted sample is much greater than the frequency of the sampling rate. A CRM device typically determines that a heart beat has occurred when a voltage threshold is attained by the sensed signal. However, a signal that is sampled at a relatively low rate and that has interference or noise from the MRI machine can produce smoothed voltage traces that are either below the trigger threshold when the heart actually beats or that are above the voltage threshold when the heart has not actually beat. Where a heart beat is not sensed, such as where interference causes the trigger threshold to not be satisfied, the CRM device may determine that the heart has not beat in the appropriate time interval despite the fact that it actually had beat, and may initiate a pacing pulse. Such a pacing pulse would conflict with the heart's naturally produced heart beat and could have detrimental effects on the patient. Moreover, in the case of a patient with tachycardia or undergoing fibrillation, the CRM device may not detect the existence of fast or irregular heart beats and may not properly initiate therapy. This could result in cardiac fibrillation and consequent injury to the patient.

Some existing CRM devices solve the problem of sensing a heart beat in the presence of LFIC by having a switch that can be actuated (such as through telemetry) to set the CRM device to an asynchronous mode where the CRM device initiates a beat at regular intervals without sensing cardiac activity. However, asynchronous modes of operation can be sub-optimal. For example, if a patient experiences fibrillation while the CRM device is set to an asynchronous mode, then the patient will not receive the appropriate defibrillation therapy. Embodiments of the present invention include CRM devices that are capable of operating properly within an MRI machine and sensing a patient's cardiac activity despite the presence of LFIC.

An embodiment of the present invention includes sampling a cardiac signal at a relatively high rate, such as equal to or greater than about 8 kHz, and using digital signal processing to produce a signal that can be used to detect the patient's cardiac activity despite the presence of MRI-induced noise.

Figure 5:
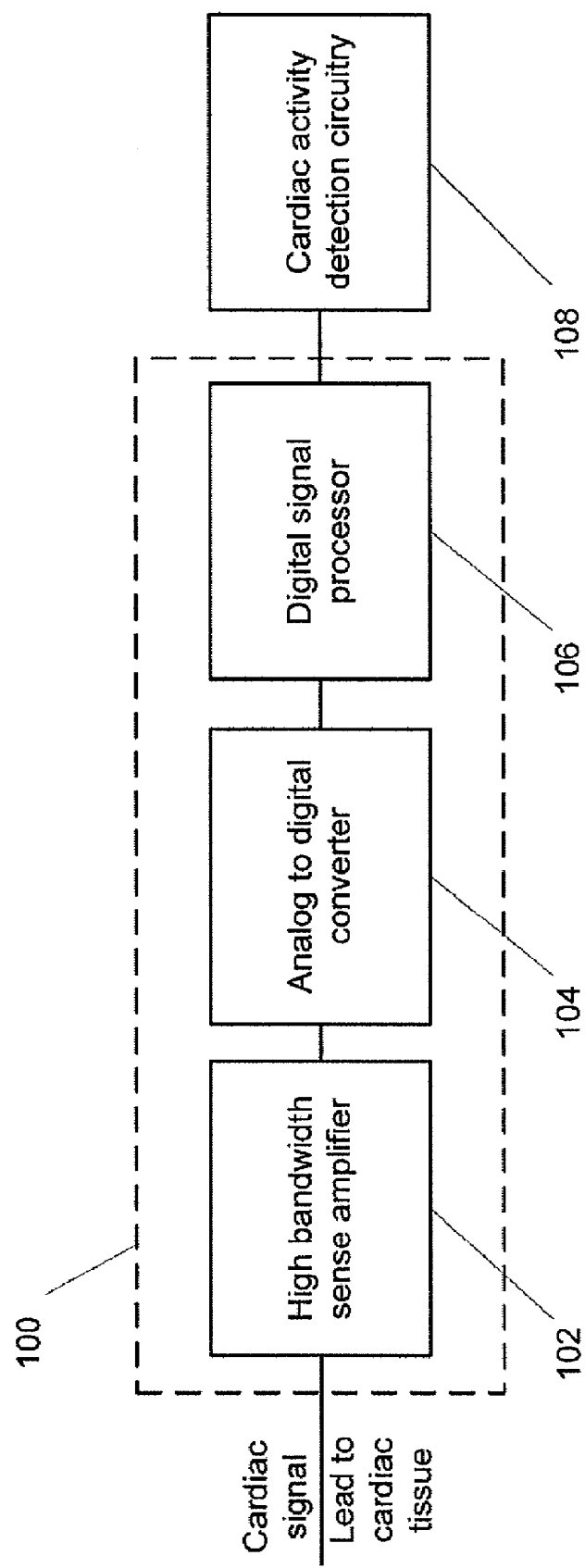
FIG. 5 is a schematic of signal processing circuitry for use in an implantable medical device constructed according to the principles of the present invention.

An embodiment of signal processing circuitry of a CRM device is shown in FIG. 5. CRM device includes signal processing circuitry 100, as shown also in FIG. 2. Signal processing circuitry 100 is typically located within a housing of a CRM device. In the embodiment of FIG. 5, circuitry 100 includes a high bandwidth sense amplifier 102 in electrical communication with one of conductors 40, 42 (shown in FIG. 2). In this way, high bandwidth sense amplifier 102 receives a cardiac signal that travels from the cardiac tissue, through one of conductors 40, 42, and to high bandwidth sense amplifier 102. High bandwidth sense amplifier 102 has a high bandwidth, such as equal to or greater than 4 kHz, for supporting a high sampling rate and high data flow rate. For example, the amplifier can be one with a frequency response from near DC to 4 kHz or more. In some embodiments, sense amplifier 102 has a bandwidth of about 4 kHz to about 20 kHz. In some embodiments, the sense amplifier 102 has a bandwidth of about 7 kHz. In some embodiments, the sense amplifier 102 has a bandwidth of about 5 kHz to about 7 kHz. The components of sense amplifier 102 are selected according to knowledge available to those of skill in the art to produce a sense amplifier 102 having high bandwidth. For example, various embodiments of sense amplifiers for use in a CRM device are disclosed in U.S. Pat. Nos. 6,016,446 and 6,427,085, which are herein incorporated by reference in their entirety. High bandwidth sense amplifier 102 is a receive amplifier that is used to amplify the electrogram signals received through conductors 40, 42.

The signal processing circuitry 100 further includes an analog-to-digital converter (ADC) 104 to digitize the analog cardiac signal that is output from the sense amplifier 102. The ADC 104 converts the continuous analog cardiac signal to discrete digital numbers. An ADC is generally characterized as having a resolution, which is the number of discrete values it can produce for a given range of input values. Resolution is also described as the number of quantization levels. For example, an ADC may have 256 quantization levels, which would mean that the ADC would encode an analog signal to a digital number that has a resolution of $1/256^{th}$ of the range of possible analog values. An ADC also has a sampling rate or sampling frequency which is the time interval between successive conversions of the analog signal to a digital number. Because the analog signal is continuous and a digital number is discrete, the ADC reduces the continuous signal to discrete numbers that have some time interval between them. ADC 104 is generally configured to have a relatively high sampling rate. In some embodiments, ADC 104 has a sampling rate that is equal to or greater than twice the bandwidth of sense amplifier 102. In some embodiments, the sampling rate of ADC 104 is equal to or greater than about 8 kHz. In some embodiments, ADC 104 may have a sampling rate of about 10 kHz to about 20 kHz. In some embodiments, the sampling rate of ADC 104 is equal to about 20 kHz. In some embodiments, ADC 104 may have a sampling rate of about 8 kHz to about 100 kHz.

After the analog signal is converted to a digital signal by ADC 104, the digital signal is processed using a digital signal processor 106. Digital signal processor 106 may be constructed from electronic components known to those of skill in the art for providing digital signal processing. Generally, digital signal processor 106 is a dedicated integrated circuit. Many suitable digital signal processors are available commercially, such as from Texas Instruments (Dallas, Tex.) and Analog Devices (Norwood, Mass.).

Digital signal processor 106 may be configured to utilize any of a number of different digital signal processing techniques. In one embodiment, the digital signal processing comprises linear filtration of the digital signal. For example, a linear filter implemented by digital signal processor 106 can be a low-pass filter that passes only low frequencies such as those frequencies that are typical of a cardiac signal and that blocks higher frequencies such as those associated with LFIC from an MRI machine. The linear filter may also be a band pass filter that passes only a limited range of frequencies such as those frequencies that are typical of a cardiac signal and blocks other frequencies such as the frequencies that are associated with an MRI environment. Other types of linear filtering are usable.

In a further embodiment, the digital signal processing technique may comprise non-linear filtration. There are many usable embodiments of a non-linear filter. For example, one exemplary non-linear filter is a phase-locked loop (PLL), which is a closed-loop feedback control system that generates and outputs a signal in relation to the frequency and phase of the input cardiac signal. A phase-locked loop circuit responds to both the frequency and the phase of the input cardiac signal, automatically raising or lowering the frequency of a controlled oscillator until it is matched to the reference in both frequency and phase. Other types of non-linear filtering are usable.

In yet another embodiment, the digital signal processing technique may comprise a transform technique. There are many usable transform techniques. One exemplary transform technique is a Fourier transform. A typical Fourier transform decomposes a function into a continuous spectrum of its frequency components, and then an inverse transform can be used to synthesize a function from its spectrum of frequency components. A Fourier transform can be used to determine whether a sample of the cardiac signal includes interference such as interference associated with an MRI machine. Another use for a Fourier transform is to determine if a sample taken at a low sampling rate has the same frequency content as a sample taken at a high sampling rate. By way of example, an occasional sample may be taken at a high sampling rate and compared with another sample taken at a lower sampling rate, such as a known good sample or a recently taken sample. If the Fourier transform of the high sampling rate sample has a significantly different frequency spectrum, then it may be inferred that interference is present, possibly from an MRI machine, and that the CRM device should operate at a high frequency sampling mode until a later Fourier transform reveals that the frequency spectra of a high frequency and a low frequency sample are approximately the same.

Furthermore, the digital signal processing technique may comprise a wavelet transform. A wavelet transform is a representation of a signal in terms of a finite length or fast decaying oscillating waveform. This waveform is scaled and translated to match the input signal. Such a wavelet transform may be used in a similar manner to a Fourier transform.

Another usable digital signal processing technique is to utilize a basis function. This involves creating a sample signal that simulates an intended or expected signal, where this ideal sample signal is called the basis function. For example, a basis function can be built from known good samples collected over time. Then a sampled signal can be compared against the basis function to determine whether the signal is distorted, such as would be present in an MRI machine, or if the signal is not distorted.

The digital signal processing techniques could also comprise a heuristic technique. A heuristic technique is one that is based on finding a solution that works for a broad collection of data. A heuristic technique solves a problem empirically without necessarily determining the reason why it works.

It should be noted that slew rate limiting is generally not a sufficient digital signal processing technique by itself. This is because the slew rate of interference created by the MRI machine in certain modes of operation can be the same or similar to the slew rate of cardiac signals. Therefore, slew rate limiting that is configured to remove certain MRI interference could also remove desirable cardiac signals. However, in some embodiments, slew rate limiting may be a component of the digital signal processing to remove portions of a sensed signal that are clearly outside of the frequency of the expected cardiac signal.

Digital signal processor 106 uses digital signal processing techniques, such as those described herein, to process a high-frequency sequence of samples. In some embodiments, the digital signal processing techniques are used to identify artifacts or interference within a signal that is characteristic of MRI interference. In some embodiments, the digital signal processing techniques are used to create a separate high-frequency sequence of samples where the signal artifact that is characteristic of MRI interference has been reduced with respect to the high-frequency sequence of samples before processing. This separate high-frequency sequence of samples is generally continuous in time and allows other circuitry in the CRM device to detect the presence of a heart beat despite of the presence of MRI-induced interference. Being generally continuous in time means that the sample has a unique value present at each time interval that corresponds to the sampling rate of the analog to digital converter 104. The sample is not blanked out or artificially held constant for certain time intervals where interference is present.

As shown in FIG. 5, a signal from digital signal processor 106 is sent to a cardiac activity detection circuit 108. The signals sent to cardiac activity detection circuit 108 are generally the high frequency samples that have had the signal artifact that is characteristic of MRI interference reduced. This signal can then be processed by cardiac activity detection circuit 108 in a conventional manner to detect cardiac activity. Because the signal artifact characteristic of MRI interference has been substantially reduced, the cardiac activity detection circuit is generally capable of accurately determining the cardiac activity despite the fact that the CRM device is subject to MRI-induced interference.

Figure 6:
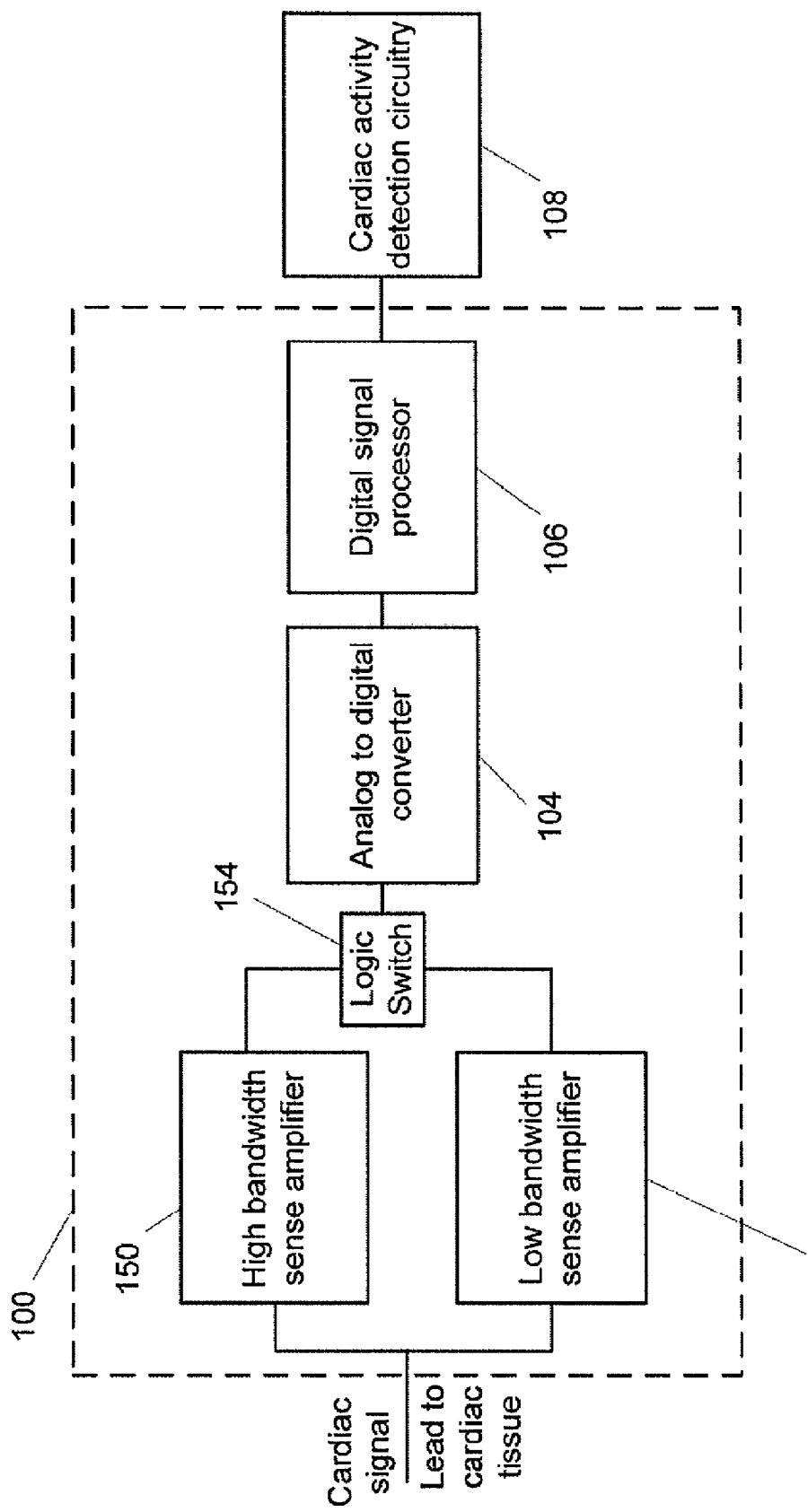
FIG. 6 is a schematic of an alternative embodiment of the signal processing circuitry of FIG. 5.

An alternative embodiment is depicted in FIG. 6. In the embodiment of FIG. 6, there are two sense amplifiers 150, 152. Sense amplifier 150 has a relatively high bandwidth and sense amplifier 152 has a relatively low bandwidth. For example, sense amplifier 150 may be configured having a relatively high bandwidth, such as equal to or greater than 4 kHz, and sense amplifier 152 may be configured having a relatively low bandwidth, such as equal to or lower than 1 kHz, or in some embodiments, about 200 Hz. A logic switch 154 is provided to select between high bandwidth sense amplifier 150 and low bandwidth sense amplifier 152. In some embodiments, there may be three or more sense amplifiers provided, such as sense amplifiers having relatively low, medium, and high bandwidth. Various components or elements of the various sense amplifier circuits may be shared, or each sense amplifier may include a circuit that is separate from any others.

There are many possible strategies for switching between the sense amplifiers 150, 152. In one strategy, a sensor is provided that can be used to detect the presence of a magnetic field that is characteristic of MRI. For example, the sensor can be a magnetometer, a Hall-effect sensor, or a reed switch that is configured to enable detection of the strong magnetic field associated with MRI, which can be on the order of 1,000 to 30,000 gauss, and to differentiate the MRI magnetic field from the earth's ambient magnetic field, which is generally less than 1 gauss. When the output of this type of sensor indicates the presence of an MRI event, logic switch 154 can switch from low bandwidth sense amplifier 152 to high bandwidth sense amplifier 150. In another strategy, a sensor is provided to detect the presence of LFIC, such as LFIC generated by an MRI environment. For example, an LFIC sensor can be a Hall effect sensor or can be a sensor that measures the voltage differential across a small resistor. When such as sensor detects LFIC, switch 154 can switch from low bandwidth sense amplifier 152 to high bandwidth sense amplifier 150. In yet another strategy, a signal is sent by telemetry to initiate a switch. For example, a physician or other person who knows that a patient will be undergoing an MRI procedure may send a signal that causes the high bandwidth sense amplifier to be utilized, until the MRI procedure is completed at which point an additional signal will be transmitted to cause the device to switch to the low bandwidth sense amplifier. In further embodiments, an occasional sample of cardiac signal will be taken by the high bandwidth sense amplifier 150, and this sample will be processed, such as by a Fourier transform, to determine whether interference is present. If so, then switch 154 will be switched to utilize high bandwidth sense amplifier 150 until the interference is no longer present.

As discussed above, an important consideration associated with implanted medical devices is the desire to maximize battery life. A high bandwidth sense amplifier will consume more electric power than a low bandwidth sense amplifier.

Therefore, having a switch such as switch 154 to switch between high bandwidth and low bandwidth sense amplifiers can help to optimize battery life so that the high bandwidth sense amplifier 150 is utilized substantially only when MRI induced interference is present.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

The above specification provides a complete description of the structure and use of the invention. Since many of the embodiments of the invention can be made without parting from the spirit and scope of the invention, the invention resides in the claims.

What is claimed is:

1. A method of determining a heart rate from a physiological electrical signal received in an implantable medical device, the method comprising:
   (i) receiving an input associated with the presence of an environment that tends to cause corruption of a physiological electrical signal; and
   (ii) initiating a mode of operation for reducing corruption of the physiological electrical signal, the mode of operation comprising
       (a) providing a high and a low bandwidth amplifier in an implantable medical device, wherein the high bandwidth amplifier has a bandwidth of at least 4 kHz and the low bandwidth amplifier has a bandwidth equal no greater than 1 kHz;
       (b) providing a switch configured to select between the high bandwidth and low bandwidth amplifiers, wherein the switch is switched to utilize the high bandwidth amplifier if corruption of the physiological electrical signal is detected;
       (c) amplifying the physiological electrical signal with the selected amplifier;
       (d) sampling the amplified physiological electrical signal at a sampling frequency of at least 8 kHz to obtain a first sequence of samples;
       (e) processing the first sequence of samples to identify a superposed signal artifact characteristic of MRI interference;
       (f) reducing the superposed signal artifact from the first sequence of samples to form a second sequence of samples; and
       (g) processing the second sequence of samples to identify the timing of heart contractions.

2. The method of claim 1, where the environment that tends to cause corruption of a physiological electrical signal comprises magnetic resonance imaging.

3. The method of claim 1, where the input comprises receiving a signal by telemetry.

4. The method of claim 3, where the telemetric signal is initiated by a person who is aware of the presence of an environment that tends to cause corruption of an electrical signal.

5. The method of claim 1, where the input comprises receiving a signal from a magnetic field sensor.

6. The method of claim 1, where the input comprises receiving a signal from a sensor configured to measure induced currents within a conductive loop.

7. A method for reducing MRI interference from a physiological electrical signal received in an implantable medical device, the method comprising:
   providing a high and a low bandwidth amplifier in an implantable medical device, wherein the high bandwidth amplifier has a bandwidth of at least 4 kHz and the low bandwidth amplifier has a bandwidth equal no greater than 1 kHz;
   providing a switch configured to select between the high bandwidth and low bandwidth amplifiers, wherein the switch is switched to utilize the high bandwidth amplifier if corruption of the physiological electrical signal is detected;
   amplifying the physiological electrical signal with the selected amplifier;
   sampling the amplified physiological electrical signal at a sampling frequency of at least 8 kHz to obtain a first sequence of samples;
   processing the first sequence of samples to identify a signal artifact characteristic of MRI interference; and
   creating a second sequence of samples by reducing the signal artifact characteristic of MRI interference from the first sequence of samples, the second sequence continuous in time.

8. The method of claim 7, where the step of sampling the physiological electrical signal comprises sampling the signal at a frequency between about 8 kHz and 100 kHz.

9. The method of claim 7, where the step of processing the first sequence of samples comprises using digital signal processing techniques.

10. The method of claim 9, where the digital signal processing technique comprises linear filtering.

11. The method of claim 9, where the digital signal processing technique comprises non-linear filtering.

12. The method of claim 9, where the digital signal processing technique comprises a heuristic technique.

13. The method of claim 7, further comprising the step of determining cardiac activity from the second sequence of samples.

14. The method of claim 7, where the step of sampling the amplified physiological electrical further comprises converting the amplified signal from analog to digital.

15. A method of calculating a heart rate from a physiological electrical signal received in an implantable medical device, the method comprising:
   providing a high and a low bandwidth amplifier in an implantable medical device, wherein the high bandwidth amplifier has a bandwidth of at least 4 kHz and the low bandwidth amplifier has a bandwidth equal no greater than 1 kHz;
   providing a switch configured to select between the high bandwidth and low bandwidth amplifiers, wherein the switch is switched to utilize the high bandwidth amplifier if corruption of the physiological electrical signal is detected;
   amplifying the physiological electrical signal with the selected amplifier;
   sampling the amplified physiological electrical signal at a sampling frequency of at least 8 kHz to obtain a first sequence of samples;
   processing the first sequence of samples to identify a superposed signal artifact characteristic of MRI interference;
   reducing the superposed signal artifact from the first sequence of samples to form a second sequence of samples; and
   processing the second sequence of samples to identify the timing of heart contractions.

16. The method of claim 15, where the step of sampling the physiological electrical signal comprises sampling the signal at a frequency between about 8 kHz and 100 kHz.

17. The method of claim 15, where the step of processing the first sequence of samples comprises using digital signal processing techniques.

18. The method of claim 17, where the digital signal processing technique comprises linear filtering.

19. The method of claim 17, where the digital signal processing technique comprises non-linear filtering.

20. The method of claim 17, where the digital signal processing technique comprises a heuristic technique.

21. The method of claim 15, where the step of sampling the amplified physiological electrical signal further comprises converting the amplified signal from an analog signal to a digital signal.

22. An implantable medical device that receives and processes a physiological electrical signal, the implantable medical device comprising:

(i) a conductor for transmitting the physiological electrical signal from body tissue to the implantable medical device;

(ii) physiological signal processing circuitry for identifying heart contractions from the physiological electrical signal, the signal processing circuitry including:

(a) a first amplifier for amplifying the physiological electrical signal received from the conductor having a bandwidth of at least 4 kHz;

(b) a first analog to digital converter for sampling the amplified physiological electrical signal at a sampling frequency of at least 8 kHz to obtain a first sequence of samples;

(c) a digital signal processor configured to process the first sequence of samples to identify a superposed signal artifact characteristic of MRI interference and further configured to reduce the superposed signal artifact from the first sequence of samples to form a second sequence of samples; and (d) cardiac activity detection circuitry configured to process the second sequence of samples to identify heart contractions;

(iii) a sensor configured to detect the presence of an environment that tends to cause corruption of a physiological electrical signal;

(iv) a second amplifier for amplifying the physiological electrical signal received from the conductor;

(v) a second analog to digital converter for sampling the amplified physiological electrical signal from the second amplifier at a sampling frequency less than about 1 kHz; and (vi) a switch to selectively couple either the first analog to digital converter or the second analog to digital converter to the digital signal processor, where the switch is configured to couple the first analog to digital converter to the digital signal processor in response to the detection of the presence of an environment that tends to cause corruption of a physiological electrical signal.

* * * * *

UNITED STATES PATENT AND TRADEMARK OFFICE
CERTIFICATE OF CORRECTION

| | | |
|---|---|---|
| PATENT NO. | : 7,853,318 B2 | Page 1 of 1 |
| APPLICATION NO. | : 11/686159 | |
| DATED | : December 14, 2010 | |
| INVENTOR(S) | : Wedan | |

It is certified that error appears in the above-identified patent and that said Letters Patent is hereby corrected as shown below:

Claim 1, line 13: "the low bandwidth amplifier has a bandwidth equal --to-- no"

Claim 7, line 7: "low bandwidth amplifier has a bandwidth equal --to-- no"

Claim 15, line 7: "low bandwidth amplifier has a bandwidth equal --to-- no"

Signed and Sealed this
Tenth Day of May, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,853,318 B2 | Page 1 of 1 |
| APPLICATION NO. | : 11/686159 | |
| DATED | : December 14, 2010 | |
| INVENTOR(S) | : Wedan | |

It is certified that error appears in the above-identified patent and that said Letters Patent is hereby corrected as shown below:

Column 11, line 33 (Claim 1, line 13) "the low bandwidth amplifier has a bandwidth equal --to-- no"

Column 12, line 7 (Claim 7, line 7) "low bandwidth amplifier has a bandwidth equal --to-- no"

Column 12, line 49 (Claim 15, line 7) "low bandwidth amplifier has a bandwidth equal --to-- no"

This certificate supersedes the Certificate of Correction issued May 10, 2011.

Signed and Sealed this
Thirty-first Day of May, 2011

David J. Kappos
*Director of the United States Patent and Trademark Office*